US012796910B2

(12) United States Patent
Blocher et al.

(10) Patent No.: US 12,796,910 B2
(45) **Date of Patent: *Nov. 17, 2026**

(54) OPTOMETER FOR HOME USE

(71) Applicant: Alexandra Blocher, Mercer Island, WA (US)

(72) Inventors: Alexandra Blocher, Mercer Island, WA (US); Jan Hoogland

( * ) Notice: Subject to any disclaimer, the term of this patent is extended or adjusted under 35 U.S.C. 154(b) by 203 days.

This patent is subject to a terminal disclaimer.

(21) Appl. No.: 18/744,383

(22) Filed: Jun. 14, 2024

(65) Prior Publication Data

US 2024/0407641 A1 Dec. 12, 2024

Related U.S. Application Data

(63) Continuation-in-part of application No. 16/987,271, filed on Aug. 6, 2020, now abandoned, which is a continuation-in-part of application No. 16/746,309, filed on Jan. 17, 2020, now abandoned, which is a continuation of application No. 16/164,797, filed on Oct. 19, 2018, now Pat. No. 10,537,241.

(51) Int. Cl.

| | |
|---|---|
| ***A61B 3/028*** | (2006.01) |
| ***A61B 3/00*** | (2006.01) |
| ***A61B 3/06*** | (2006.01) |
| ***A61B 3/09*** | (2006.01) |
| *A61B 3/08* | (2006.01) |

(52) U.S. Cl.

CPC ............ *A61B 3/028* (2013.01); *A61B 3/0008* (2013.01); *A61B 3/0016* (2013.01); *A61B 3/06* (2013.01); *A61B 3/09* (2013.01); *A61B 3/08* (2013.01)

(58) Field of Classification Search

CPC ..... A61B 3/028; A61B 3/0008; A61B 3/0016; A61B 3/06; A61B 3/09; A61B 3/08; A61B 3/103

USPC .......................................................... 351/222

See application file for complete search history.

(56) References Cited

U.S. PATENT DOCUMENTS

| | | | | |
|---|---|---|---|---|
| 3,843,240 | A | 10/1974 | Cornsweet | |
| 4,607,923 | A | 8/1986 | Task et al. | |
| 10,537,241 | B1 | 1/2020 | Hoogland | |
| 2002/0047992 | A1 * | 4/2002 | Graves | G02B 26/06 351/212 |
| 2003/0197856 | A1 | 10/2003 | Milanich | |

(Continued)

OTHER PUBLICATIONS

International Search Report and Written Opinion mailed Jan. 9, 2020 for PCT/US2019/057232.

(Continued)

*Primary Examiner* — Mohammed A Hasan

(74) *Attorney, Agent, or Firm* — Suiter Swantz IP

(57) ABSTRACT

An optometer may include a test object including a point light source and a collimator lens configured to collimate light from the point light source. The optometer may generate, for a user viewing the point light source through the collimator lens, an image of the point illumination source on a retina of an eye when the eye is in a rest position without triggering the eye to focus. A user-perceived deviation of the image of the point source from an in-focus image is indicative of visual refractive error of the user. A user may use the device with a naked eye to gauge visual refractive error of the eye or may use the device with corrective lenses to gauge the efficacy of the corrective lenses.

23 Claims, 6 Drawing Sheets

(56) References Cited

U.S. PATENT DOCUMENTS

| | | | | |
|---|---|---|---|---|
| 2010/0265463 | A1* | 10/2010 | Lai | A61B 3/0285 351/237 |
| 2012/0249769 | A1 | 10/2012 | Naba et al. | |
| 2016/0166147 | A1 | 6/2016 | Peschka et al. | |
| 2016/0174832 | A1* | 6/2016 | Winsor | A61B 3/14 351/245 |
| 2021/0015356 | A1* | 1/2021 | Hoogland | A61B 3/028 |

OTHER PUBLICATIONS

Knight, "The spectacular power of Big Lens," The Guardian, May 10, 2018, 26 pages.

* cited by examiner

OPTOMETER FOR HOME USE

CROSS-REFERENCE TO RELATED APPLICATION

This application claims the benefit of U.S. patent application Ser. No. 16/987,271 filed on Aug. 6, 2020, which claims the benefit of U.S. patent application Ser. No. 16/746,309 filed on Jan. 17, 2020, which claims the benefit of U.S. patent application Ser. No. 16/164,797 entitled A SUBJECTIVE OPTOMETER FOR HOME USE filed on Oct. 19, 2018; all of which are hereby incorporated by reference in their entirety.

TECHNICAL FIELD

The present disclosure is directed to an optometer, and more particularly, to an optometer suitable for home use.

BACKGROUND

Vision is a very precious possession. The quality of our vision is such that what we see we consider to be reality, in contrast to any other image that mankind is able to produce. It is very difficult to imagine that what we see is actually just an image projected in our brain.

Optometry is an important guardian of the quality of that image in our brain. The present state of optometry is dramatically presented in The Guardian's May 10, 2018 article, "The spectacular power of Big Lens" calls out "the accelerating degradation of our eyes" and states that "[v]ision campaigners forecast that the myopia epidemic will put enormous strain on health systems across the developing world, which are already unable to equip their populations with a medical device that has been around since the Middle Ages." This crisis calls for a reassessment of what optometry can do for us.

Optometry is concerned with the measurement of the refractive errors of the eye, such as being out of focus and astigmatism. Optometry is practiced by optometrists and ophthalmologists; the latter profession includes the ability to perform eye surgery. To obtain an assessment of the state of personal ametropia, a visit to an optometrist is presently the only option. It is a significant inconvenience and expense, as compared to other measurements of important bodily data. Considering the present occurrence of ametropia, it is very desirable to be able to make an assessment ourselves, as is done with so many other health conditions. Unfortunately, an optometer for home use to measure ametropia, that is the presence of refractive errors of the eye, is not available, although it clearly is very much needed.

It is therefore desirable to provide systems and methods for subjective measurements of the refractive errors of the eye and further for such systems and methods that may be suitable for home use. In this regard, such a system may provide similar benefits as home-use thermometers or blood pressure monitors currently available that provide users the ability to make important health decisions.

SUMMARY

The Subjective Optometer for Home Use consists of a rotational test object containing a point light source, an orientation marker and a resolution target, a focusing means and a collimator. All measurements are made by the user.

BRIEF DESCRIPTION OF DRAWINGS

The numerous advantages of the disclosure may be better understood by those skilled in the art by reference to the accompanying figures.

DETAILED DESCRIPTION

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Embodiments of the present disclosure are directed to systems and methods for a user to subjectively assess refractive errors of his or her eyes such as, but not limited to focal errors or astigmatism. This assessment may be used for multiple purposes. For example, a subjective assessment of refractive errors may be suitable for determining required parameters for corrective lenses (e.g., corrective lenses that may be ordered online and/or by mail). By way of another example, this assessment may be used for diagnostic purposes such as evaluating a current set of corrective lenses or tracking changes in vision over time.

Figure 1:
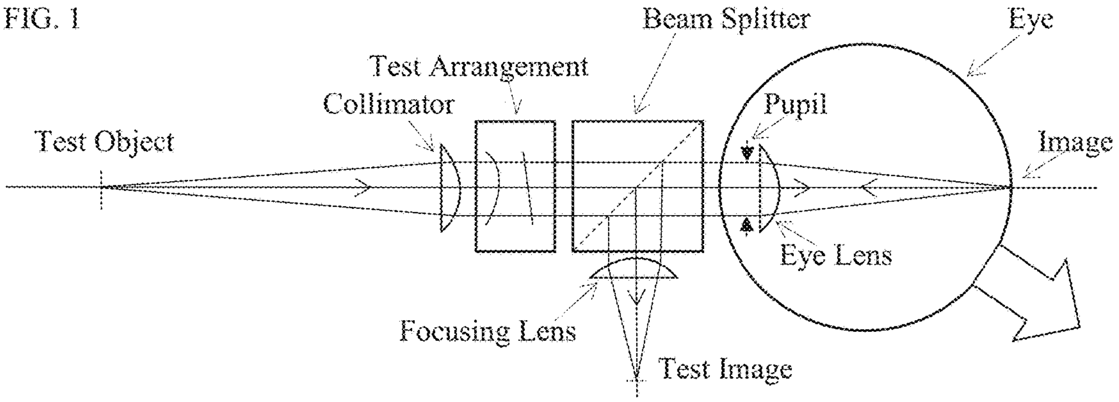
FIG. 1 is a schematic view of an objective autorefractor in accordance with the present state of the art.

It is contemplated herein that ametropia, or measurements of refractive errors in the eye, may be measured objectively or subjectively. Objective measurements may be performed by an optometer (e.g., an autorefractor) in which the image assessment is based on electronic processing. FIG. 1 is a schematic view of an objective autorefractor in accordance with one or more embodiments of the present disclosure. A test arrangement may produce an image on the retina, and the reflection of this image on the retina is made accessible via a beam splitter for processing. In this regard, an objective optometer may assess refractive errors in the eye without assistance from an optometrist or the patient.

A pervasive problem with the objective approach is that the quality of the retina as a reflective projection screen may be exceedingly poor. This is to be expected because it is a transmission screen, not a reflective projection screen. This poor quality of the reflected test image on the retina limits the accuracy of the objective test method and incurs considerable complexity and expense to obtain acceptable accuracy of the measurements. The unsuitability of the retina as a reflective projection screen is thus a major and unavoidable limitation of the objective measurement of refractive errors.

Because an objective measurement may lack accuracy or reliability, it is often followed up in practice by a subjective method of measuring the refractive errors. Subjective measurements typically rely on input from the patient to assess a quality of an image. For example, a typical subjective measurement consists of an examination by the optometrist by means of a phoropter and is regarded as a fine-tuning of the measurement provided by the autorefractor. The examination relies on the opinion of the patient on the image quality of the characters presented.

It is further contemplated herein that traditional subjective measurements have the following deficiencies:

- The inexperience or haphazardness of the patient to evaluate a complex image.
- The use of characters for the test, which engages the accommodation of the eye.
- The occurrence of instrument myopia and situation myopia.
- The large amount of time and patience required to arrive at a final evaluation.
- The evaluation needs to take place at a relatively high level of illumination, which reduces the operating aperture of the eye.
- Optometric service is out of reach for the majority of people in this world, both financially and physically.

For this reason, optometrists typically currently use a combination of objective and subjective methods together to provide a prescription for corrective glasses of sufficient accuracy and reliability. However, considering the present state of ametropia globally as well as issues surrounding access to quality eye care, a subjective optometer for home use that provides accurate and reliable assessment of the refractive errors of the eye is very much needed.

Embodiments of the present disclosure are directed to a subjective optometer having a test object with a diffraction-limited feature and a collimator (e.g., a lens) to collect light from the test object and direct the light to the eye. In this regard, the eye may remain in a state of rest during the measurement to provide an accurate assessment of the natural refractive errors in the eye. In particular, the perceived size and shape of the diffraction-limited feature projected onto the retina may be indicative of the refractive errors in the eye. Further, the light intensity, color, and numerical aperture of the system may be adjustable by the user (e.g., manually controllable, numerically controllable, or the like) to adjust the conditions of the measurement. Accordingly, a patient (e.g., a user) may make accurate subjective measurements of refractive errors of his or her eyes, which is the only way to assess the image quality to the limit of the resolution capability of the eye. Further, the systems and methods disclosed herein employs the superior accuracy of the subjective method over the accuracy of the objective method and overcomes all the deficiencies of the traditional examination by means of a phoropter.

Referring now to FIGS. 2-6, a subjective optometer is described in greater detail in accordance with one or more embodiments of the present disclosure.

Figure 2:
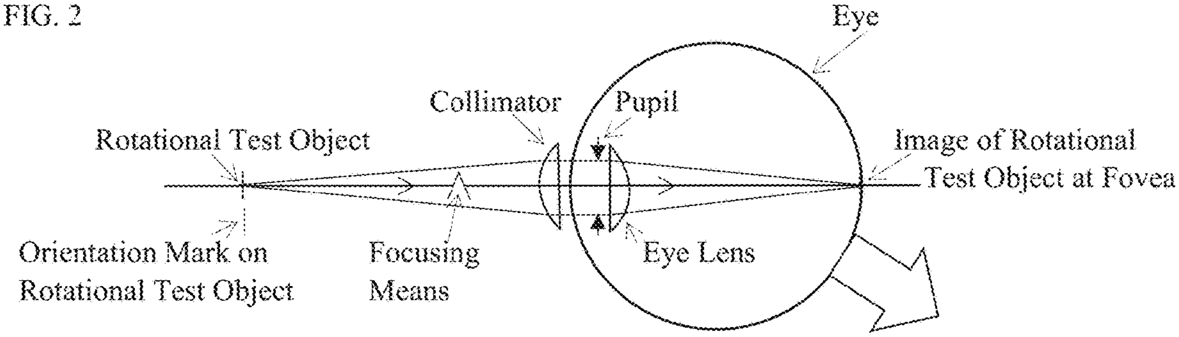
FIG. 2 is a schematic view of a subjective optometer in accordance with one or more embodiments of the present disclosure.

FIG. 2 is a schematic view of a subjective optometer in accordance with one or more embodiments of the present disclosure. The subjective optometer is based on the judgment of the user to assess the image quality of the test object on the retina. This arrangement evaluates an image to the resolution limit of the eye.

In another embodiment, the subjective optometer includes a collimator (e.g., a lens) to collect light from a test object and direct the light into an eye. In this regard, the combination of the collimator and an eye lens within the eye may project an image of the test object onto the retina of the eye. In one embodiment, the collimator is positioned to collimate light from the test object. In this regard, the eye lens may view the test object as if it were at an infinite distance from the eye.

In another embodiment, the subjective optometer (e.g., a subjective optometer for home use) includes a test object including at least one diffraction-limited feature that prevents the eye from focusing (e.g., the eye lens remains in a rest position) when viewing the test object. In particular, the image of the diffraction-limited feature lacks detail that would trigger the eye to focus. The use of a diffraction-limited test object thus greatly reduces the subjectivity of the evaluation of the image quality because the only requirement of the user is to determine the smallest line width of the image.

Figure 3:
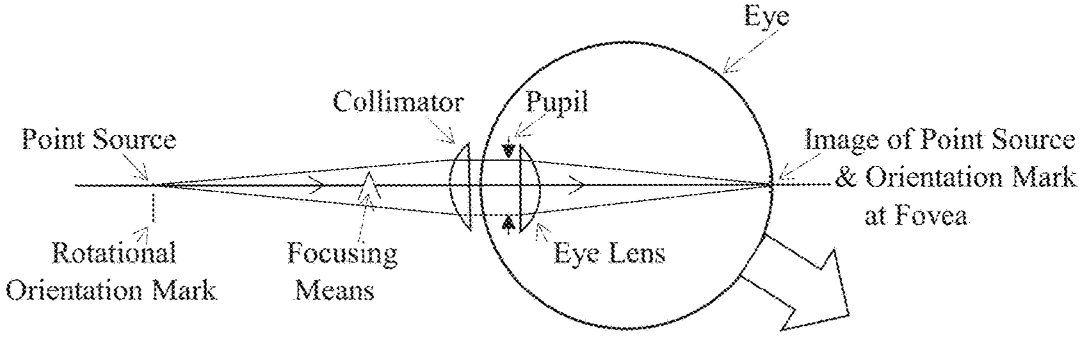
FIG. 3 is a schematic view of the subjective optometer including a test object with a point source in accordance with one or more embodiments of the present disclosure.

In one embodiment, a diffraction-limited feature includes a point light source (e.g., a pin-hole light source, or the like). A point source as a test object is a light emitting area of sufficiently small size and shape as to not significantly degrade the intended measurement at hand. For example, a normal (e.g., emmetropic) eye may perceive an image of the point light source projected to infinity with the collimator as a diffraction-limited point light source. FIG. 3 is a schematic view of the subjective optometer including a test object with a point source in accordance with one or more embodiments of the present disclosure. Further, FIGS. 4-6 also illustrate the use of a point light source. As described previously herein, characteristics of the point light source such as, but not limited to, the intensity or the color may be adjusted. For example, the subjective optometer may include one or more selectively-insertable neutral density or spectral filters to adjust the intensity and/or the color of the point light source.

In another embodiment, a diffraction-limited feature includes a diffraction-limited printed feature on the test object. For example, a diffraction-limited printed feature may include a spot having a diffraction-limited radius or a line with a diffraction-limited width.

The subjective optometer may further include one or more additional test objects (e.g., a combination of test objects) to provide multiple types of subjective measurements. In this regard, the subjective optometer may provide a correlation between the optimum test result for reading purposes and the optimum test result for other test purposes.

In one embodiment, the test object includes a rotatable orientation mark (e.g., a rotational test object, an orientation mark, a rotational orientation mark, or the like) such as, but not limited to, a line feature. This orientation mark may then be used to assess rotation-dependent refractive errors such as, but not limited to, astigmatism. For example, the user may rotate the orientation mark and identify the orientation at which the width of the rotational test feature is the smallest, which may correlate to an orientation of astigmatism in the eye.

Figure 4:
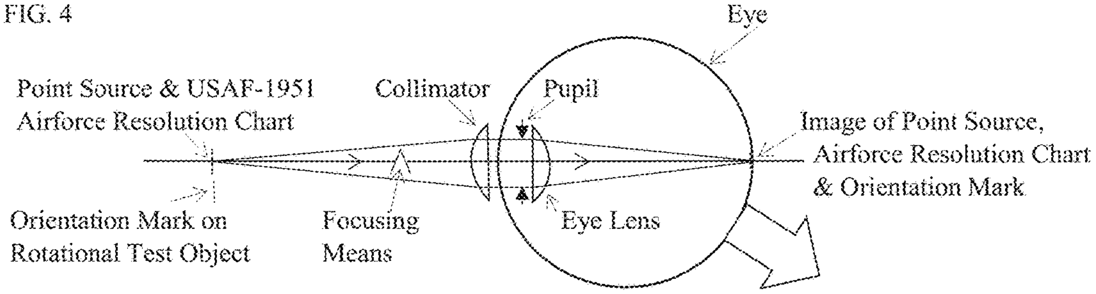
FIG. 4 is a schematic diagram of the subject optometer in which the target object includes a point light source, a resolution chart, and a rotational test feature in accordance with one or more embodiments of the present disclosure.

In another embodiment, the test object includes a resolution target to determine the optimal focus for reading material. For example, a resolution target may include multiple sets of features spaced with different separations (e.g., different spatial periods). For instance, the resolution target may include, but is not limited to, the USAF-1951 resolution chart. FIG. 4 is a schematic diagram of the subject optometer in which the target object includes a point light source, a resolution target (here depicted as a USAF-1951 resolution chart), and a rotational test feature in accordance with one or more embodiments of the present disclosure. In another embodiment, the test object includes the point light source and the resolution target (e.g., the USAF-1951 resolution target) side-by-side. In this regard, a combination target may be switchable in the optometer via a horizontal sliding mechanism where the user may shift the targets along the x-direction and selectively lock one in place, allowing the targets for multiple purposes to be housed permanently the optometer. Placing the point light source and a resolution target side-by-side in the test object provides a correlation between the optimal test results for a point light source and a test object for reading material, which provides confidence in the measurement. For example, the user's overall refractive error could be measured using a target (e.g., a multiple-pinhole target) and then the user may switch to the combination target in the test object for further validation. By way of another example, the user's overall refractive error could be measured where the multiple-pinhole target and the resolution target are simultaneously visible in the test object. In this regard, two to three test objects may be housed in the optometer. Further, these measurements may be sufficiently robust to provide a correct prescription for custom reading glasses, which is essential for online and/or mail order purposes.

Figure 5:
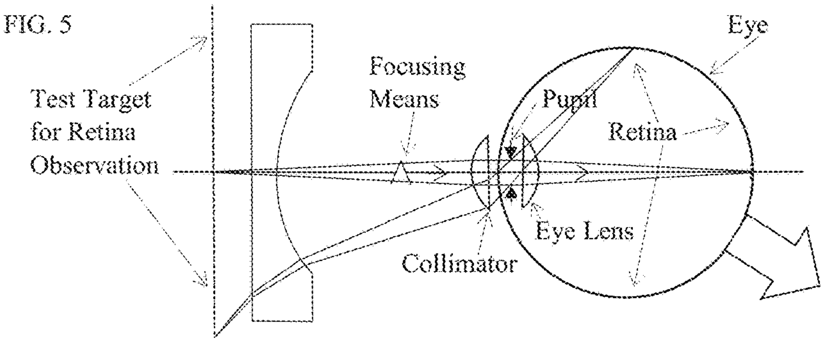
FIG. 5 is a schematic view of the subjective optometer including a test object that covers the whole retina in accordance with one or more embodiments of the present disclosure.

FIG. 5 is a schematic view of the subjective optometer including a test object that covers the whole retina in accordance with one or more embodiments of the present disclosure. Such a test object may be used to determine the field of view, the presence of glaucoma, the extent of color blindness, the extent of the fovea, the blind spot and indicate potentially problematic areas of the retina. A binocular version of the optometer provides a comparison of the two eyes, indicates alignment accuracy and shows the nature of a "lazy eye". The subjective optometer may thus provide an extensive and fascinating look into the health of the user's eyes. In some cases, a drawing of what we see can alert the optometrist and ophthalmologist in their assessment of the user's problems.

Referring now generally to FIGS. 2-6, additional features of the subjective optometer are discussed in greater detail.

In some embodiments, various measurement conditions of the subjective optometer are adjustable. For example, a numerical aperture of light directed to the eye may be adjusted (e.g., using an adjustable aperture stop, or the like). By way of another example, the intensity and/or color of the point light source or a separate light source illuminating the test target may be adjusted (e.g., using neutral density or spectral filters). This light control may provide the optimum illumination, either for optimal reading ability or for optimal accuracy to observe small changes. Further, numerical light control of the point source and the reading material test object will allow the point source test to be performed in total darkness to allow the pupil to open fully. Further, fixed test circumstances may be achieved with separate control of the light levels, numerical aperture and color, which greatly increases the repeatability of the measurements.

Figure 6:
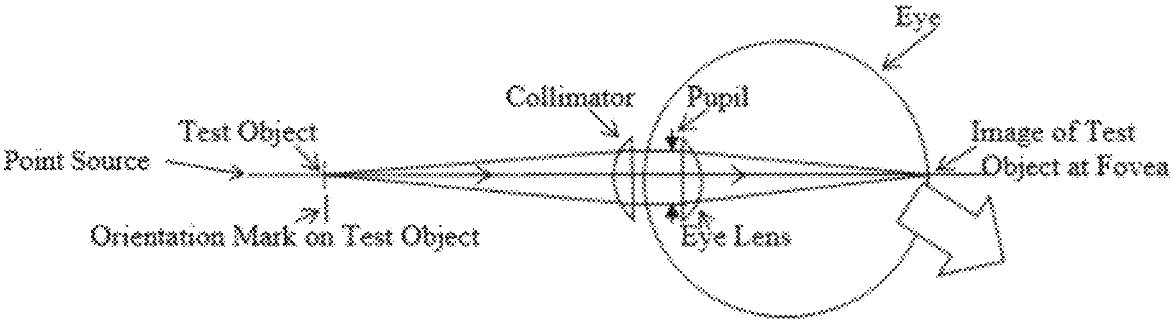
FIG. 6 is a schematic view of the subjective optimeter without a focusing means in accordance with one or more embodiments of the present disclosure.

The subjective optometer may also include a focusing means to adjust the image of the test object on the retina. Accordingly, a user may use the focusing means to focus or sharpen an image of the test object (e.g., by providing an in-focus image of the test object on the retina). Notably, the use of a diffraction-limited feature on the test object may facilitate measurements while the eye is in a rest position even when adjusting the perceived image with the focusing means. For example, configurations of the subjective optometer with a focusing means are illustrated in FIGS. 2-5. It is to be understood, however, that the subjective optometer need not include a focusing means. FIG. 6 is a schematic view of the subjective optimeter without a focusing means in accordance with one or more embodiments of the present disclosure.

In one embodiment, the focusing means includes a mechanism for adjusting a position of the collimator with respect to the test object. In this regard, the focusing means can adjust the position of at least one of the collimator or the test object. In another embodiment, the focusing means may include one or more adjustable lenses. By way of a further example, the focusing means and the collimator are integrated into a zoom lens.

Various methods for using the subjective optometer are now described in greater detail. In a general sense, the traditional limitations of subject measurements described previously herein are overcome in the subjective optometer of the present disclosure by the use of a diffraction-limited feature (e.g., a point light source) in the test object. In one embodiment, the subjective optometer presents the eye with an image of a diffraction-limited feature (e.g., a diffraction-limited point source) in the test object, which is projected at infinity by the collimator. By using a diffraction-limited feature, the eye may remain in a rest position (e.g., the eye lens may remain relaxed and adjusted for long-distance objects) and the size and shape of the image of the diffraction limited feature are indicative of refractive errors in the eye.

For example, an eye including focal errors but not astigmatism may view the diffraction-limited feature as an unfocused point, where a size of the unfocused point is indicative of focal error in the eye. In one embodiment, focal errors may be measured using a subjective optometer without a focusing means (e.g., as illustrated in FIG. 6) by noting the size of the unfocused point. For instance, the image of the point light source in this configuration may be similar to the image of a star at night. Additionally, it is noted that the user may not directly determine the sign (+ or −) of the focal errors using configuration of the optometer in FIG. 6. However, the sign may be determined by repeating the measurement while using reading glasses or prescriptive glasses having a known optical power. In some configurations, as illustrated in FIG. 6, the optometer may include a test object with a scale in order to provide a reference for measurement of the size, shape, and/or orientation of the image of the point light source. In this regard, the user may assess the magnitude of refractive errors in the eye. Additionally, the user may use the subjective optometer while wearing one or more pairs of corrective lenses. In this way, the user may identify which corrective lenses (e.g., which prescription) is most suitable or preferred.

In another embodiment, focal errors may be measured using a subjective optometer with a focusing means by adjusting the focusing means to provide the smallest observable spot corresponding to an in-focus image. Accordingly, the amount and/or direction of adjustment from a nominal position (e.g., position providing collimated light to the eye), may be indicative of sign and/or magnitude of focal errors in the eye. Further, the only subjective aspect of the measurement is the determination of the adjustment providing the smallest spot, which is very close to being objective. The absence of detail of the in-focus and out-of-focus point source images prevents accommodation of the eye. The testing at night or in a darkened room, when the eye is in its rest position, provides the optimum circumstances for high accuracy measurements and high repeatability. An accuracy of 0.12 diopter is achievable, while 0.08 diopter can be reached after some practice. These numbers are well within the accuracy required for a custom prescription and are usable for many test purposes.

For example, in the case of an eye including focal errors but no astigmatism, a diffraction-limited feature may be observed as a circle, where varying the distance between the test object and the collimator may adjust the size of the circle. Accordingly, the focal error of the eye may be measured by adjusting the distance between the test object and the collimator and noting a difference between a nominal position associated with a projection of the test object to infinity and a position at which the size of the circle is the smallest.

By way of another example, in the presence of astigmatism, a diffraction-limited feature may generally be focused to two orthogonal line images at different focal positions (e.g., different settings of the focusing means). The focal positions determine the focal errors and their difference is a measure of astigmatism. The orientations of the line images are a measure of the orientation of the astigmatism in the eye. In one embodiment, astigmatism may be generally observed in a subjective optometer without a focusing means by noting the extent of a deviation of the observed image of the diffraction-limited feature from a round spot. Further, an orientation of an elongation in the observed image may be used as an indication of the orientation of the astigmatism. For example, an orientation mark as described herein may be used to facilitate measurement of the orientation of the astigmatism.

In another embodiment, astigmatism may be measured with a subjective optometer with a focusing means by noting the settings of the focusing means that provide the two line images. In an ametropic eye having refractive errors in two orthogonal directions (e.g., an X-direction and a Y-direction), a diffraction-limited feature may be observed as an oval, where the orientation and size of the oval is indicative of the focal errors along the X and Y directions. In this case, a variation of the distance between the point source and the collimator may vary the image of the diffraction-limited feature from an oval to a diffraction-limited line image in the Y-direction, which indicates that the optical power of the eye in the X-direction is compensated. The change in distance indicates the amount of focal error of the eye in the X-direction. The focusing error in the Y-direction may be similarly detected. The difference in the locations amounts to the astigmatism of the eye. The direction of the lines indicates the orientation of the astigmatism. These data provide the prescription for the eye. Again, the only subjectivity of the measurement is the selection of the points at which the widths of the two line images are the smallest. However, this is relatively easy to determine and may be achieved with a high accuracy. In some configurations, the test object may include a scale that may be used to measure or otherwise characterize the size and/or shape of the line images at any position. In a configuration in which the focusing means is incorporated into a zoom lens, the x- and y-settings of the zoom lens when forming the two line images indicate the power prescription while an orientation of the line image indicates the orientation of the astigmatism. It is noted herein that zoom lenses are well-corrected to provide a sharp image of the test object.

An orientation mark as described herein may also be used to facilitate measurement of the orientation of the astigmatism. For example, the orientation mark may be rotated to provide the minimum line width of each of the two line images to determine the orientations of the two line images and thus the orientation of the astigmatism in the eye. By way of another example, the optometer may include an axis dial to allow the user to rotate one or more components such as, but not limited to, an orientation mark. In this way, the user may align one or more features on the orientation mark with an orientation of astigmatism to provide an accurate measure of an angular orientation of astigmatism.

Additionally, a rotatable resolution target as described herein may be used to further assess astigmatism. In a manner similar to the orientation target described above, an angular orientation of a rotatable resolution target may be adjustable using an axis dial. In particular, after angular alignment of the resolution target with the astigmatism caused by the eye, the optimum focus may be determined for each astigmatic focus. A resolution target is remarkably effective in removing the degradation of the astigmatism in each of the two orientations. The achieved resolution can be read from the resolution target and remains valid after the astigmatism has been corrected by the prescription glasses. That results in the test measuring the resolution of the eye in the case it does not have refractive errors. For example, the test may express 20/20 vision in values of the USAF-1951 Airforce Resolution Chart. The accuracy of such a resolution target is considerably better than a letter test like the Snellen Chart. The results can be compared with those obtained with the diffraction-limited feature (e.g., the point light source) tests.

In another embodiment, a zoom lens as described herein may provide adjustable focusing (e.g., variable power) along different directions. Instead of moving the collimator lens to focus the eye to determine the prescriptive power, the power may be changed by changing the power of the zoom lens in the two directions. The changes of power in the zoom lens may then indicate the required power for corrective lenses. The orientation of the astigmatism is still determined by the orientation of the line foci as described previously herein. In this case, the image plane around the image of the point source is imaged sharply in both directions.

Figure 7:
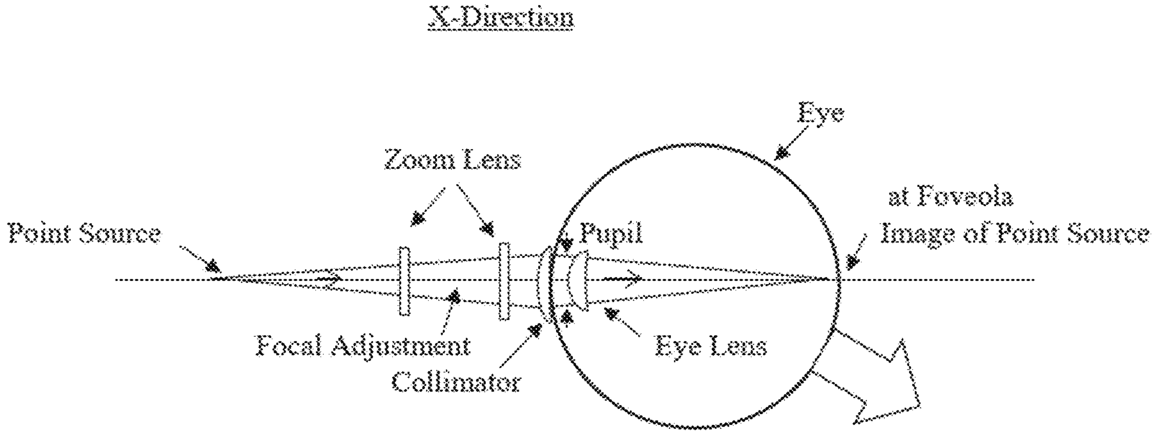
FIG. 7 is a subjective view of the subjective optometer along a first direction illustrating a zoom lens providing different adjustable focusing along two orthogonal directions in accordance with one or more embodiments of the present disclosure.
Figure 8:
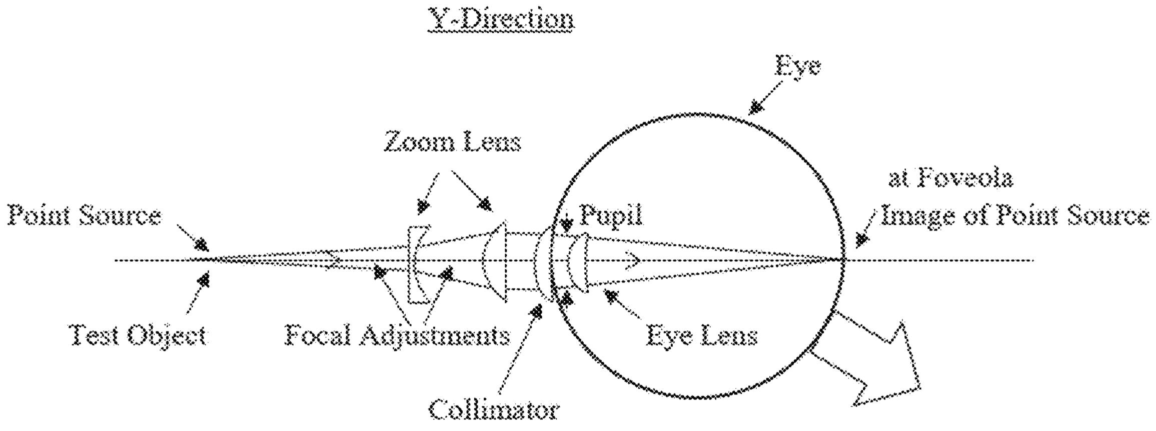
FIG. 8 is a subjective view of the subjective optometer of FIG. 7 along a second direction orthogonal to the first direction illustrating a zoom lens providing different adjustable focusing along two orthogonal directions in accordance with one or more embodiments of the present disclosure.

FIGS. 7 and 8 are subjective views of the subjective optometer illustrating a zoom lens providing different adjustable focusing along two orthogonal directions (e.g., the X and Y directions, respectively) in accordance with one or more embodiments of the present disclosure. For example, the zoom lens may include one or more cylindrical lenses oriented to provide separate focusing adjustments in the X direction (see FIG. 7), and the Y direction (see FIG. 8). Further, the subjective optometer may include, but is not required to include, one or more lenses to provide additional focusing adjustments along both directions.

Additionally, the zoom lens may be rotatable such that the X and/or Y directions may be rotated to correspond to the orientation of astigmatism in an eye. In this regard, by rotating the zoom lens to align either the X or Y directions with the orientation of the astigmatism (e.g., determined as described above), the user may then bring the entire test object into focus by adjusting the zoom lens to compensate for the astigmatism in the eye.

This procedure enables a user to verify the various corrections required (e.g., astigmatism corrections, focusing corrections, or the like) by providing a corrected image of the test object. Further, the subjective optometer can be used to check the image quality of corrective lenses at the point of optimum focus to check the correctness of the indicated prescription.

The user may then continue to adjust the various settings to provide a subjectively sharp image of the test object. Accordingly, a zoom lens configured in this way may replace a traditional phoropter (e.g., a refractor). However, the zoom lens configured in this way may provide diffraction-limited resolution, whereas a typical phoropter is limited by ⅛ diopter, which is about a factor of four worse.

In another embodiment, the optometer may include a focusing means adjusted by the user via a rotating dial collar (e.g., a power dial). The power dial may include position markings which translate the linear distance the focusing means has traveled from its nominal position to the amount of spherical or cylindrical correction needed or the measure of the user's visual refractive error. Internally, a helical cam or alternative mechanism moves the focusing means linearly along the optical axis which, depending on the specific implementation, may involve shifting the target or the collimating lens. For example, the user may, but is not limited to, adjust the power dial until it reaches its highest diopter value, rotate the axis dial until it reaches 0°, then adjust the intensity of the two or more point light sources to a comfortable level using the brightness control. The user may observe blurry circles proportionate to the type of target and the number of the two or more point light sources present. The user may then slowly rotate the power dial in the direction of decreasing diopter values. A measure of lens power prescribed to correct nearsightedness or farsightedness, or sphere value, may be indicated for a user without astigmatism when the size of the two or more point light sources are at their smallest.

In the case of a user with an astigmatism, a perceived image of the target (e.g., a multiple-pinhole target) with two or more point light sources may be viewed by the user as two or more perceived lines oriented in a common direction. The multiple-pinhole target may be rotated by the user until the two or more perceived lines become continuously oriented into one longer line.

Referring now to FIGS. 9A-9D, in some embodiments, the subjective optometer includes a rotatable multiple-pinhole target 902 with two or more point light sources 904. It is contemplated herein that it may be challenging in certain circumstances for a user to accurately gauge an orientation angle of a perceived diffraction-limited line in the presence of astigmatism. In some embodiments, a subjective optometer includes a rotatable target with the two or more point light sources 904, which is referred to herein as a multiple-pinhole target 902. In this configuration, two or more perceived lines 908 from the two or more point light sources 904 may be seen by the user and the user may rotate the multiple-pinhole target 902 to align the two or more point light sources 904 along a perceived angular orientation of the two or more perceived lines 908. In this way, the repeated instances of the two or more perceived lines 908 may assist the user with gauging an orientation of astigmatism.

Figure 9A:
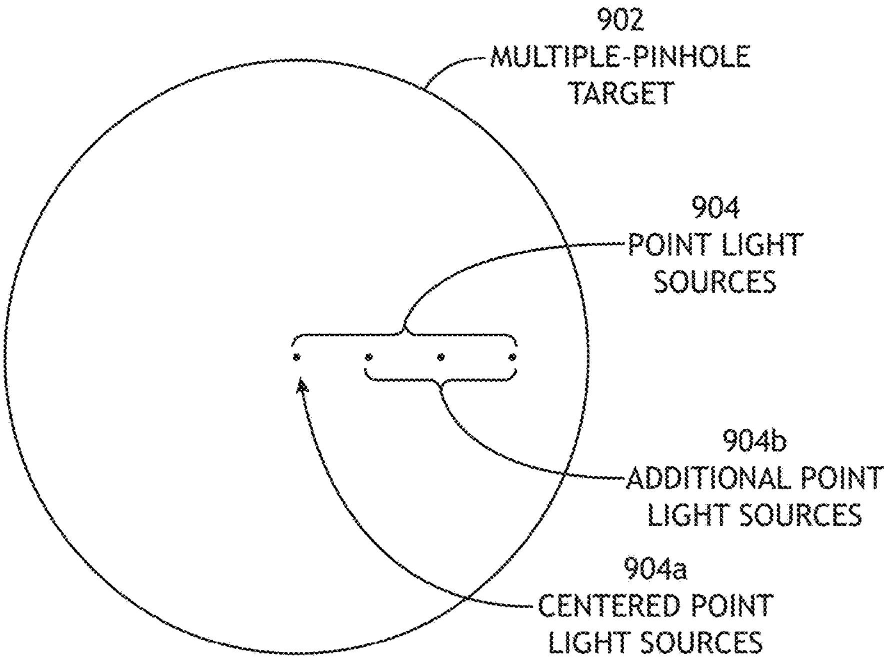
FIG. 9A is a simplified view of a multiple-pinhole target, in accordance with one or more embodiments of the present disclosure.

FIG. 9A is a simplified view of a multiple-pinhole target 902, in accordance with one or more embodiments of the present disclosure. In some embodiments, a multiple-pinhole target 902 includes a centered point light source **904*a* which is centered in the multiple-pinhole target 902 and one or more additional point light sources 904*b* distributed linearly along a radius of the multiple-pinhole target 902**.

Figure 9B:
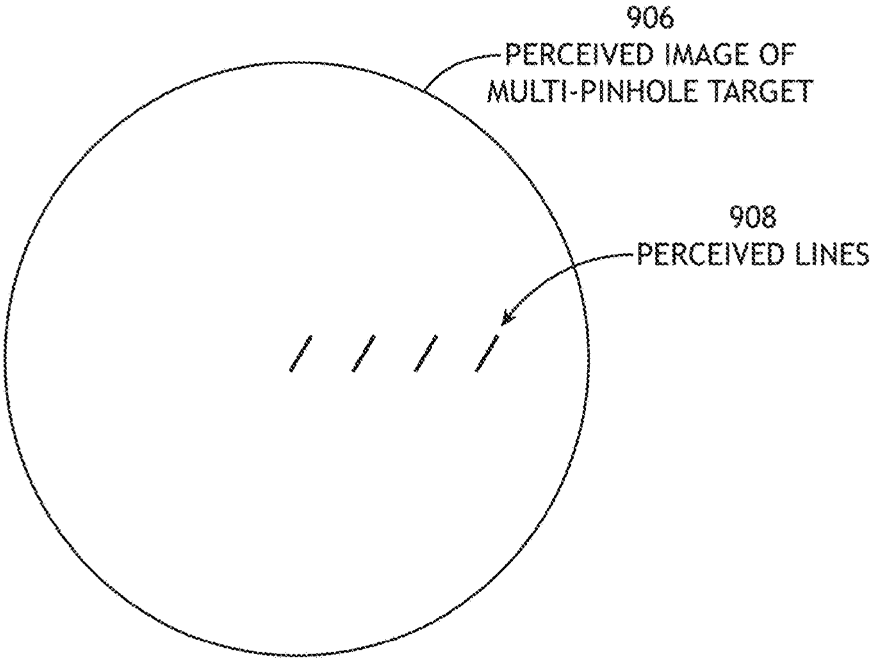
FIG. 9B is a simplified view of the perceived image of the multiple-pinhole target as perceived by a user with an astigmatism, in accordance with one or more embodiments of the present disclosure.

Measurement of an astigmatism orientation angle with the multiple-pinhole target 902 is illustrated in FIGS. 9A-9D. FIG. 9B is a simplified view of a perceived image 906 of the multiple-pinhole target 902 as perceived by a user with an astigmatism, in accordance with one or more embodiments of the present disclosure. The user may have astigmatism if, at any point during the process of adjusting the focusing means to the axis principal meridian, the user may perceive the two or more point light sources 904 appear to elongate into the two or more perceived lines 908 which appear offset and parallel. In this case, the location of the power dial at which the two or more perceived lines 908 first appear as long and thin as possible indicates the sphere value. As illustrated in FIG. 9B, the user may perceive each of the two or more point light sources 904 as the two or more perceived lines 908 oriented in a common direction associated with an orientation angle of astigmatism in a particular eye being measured.

Figure 9C:
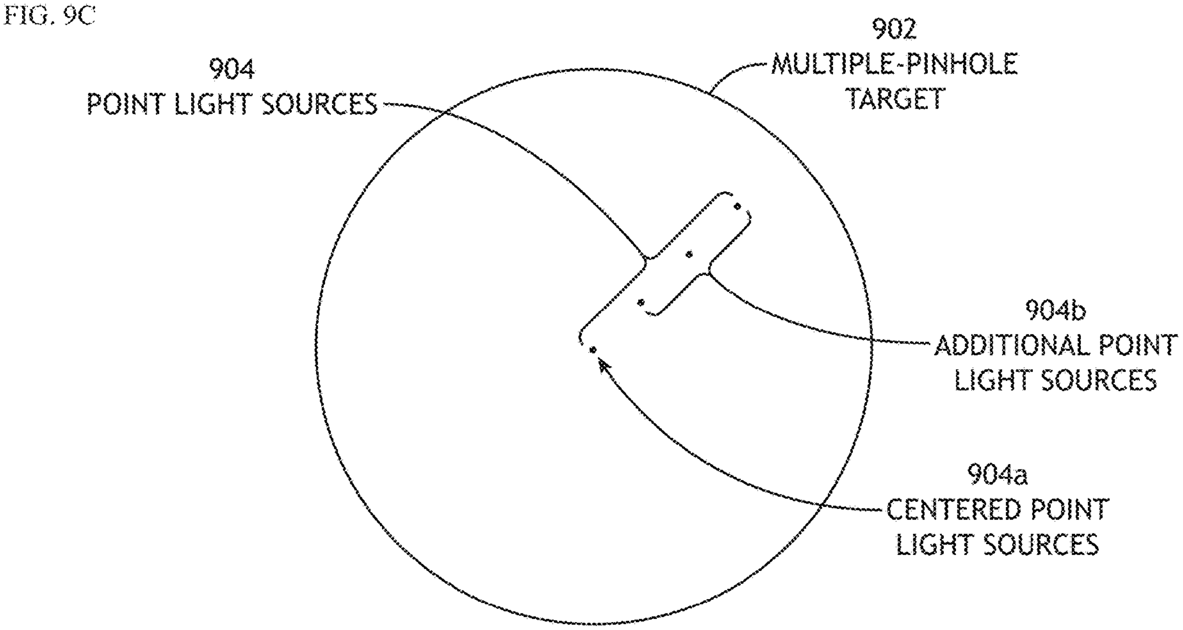
FIG. 9C is a simplified view of the multiple-pinhole target after the user adjusts an axis dial to align two or more perceived lines associated with two or more point light sources, in accordance with one or more embodiments of the present disclosure.
Figure 9D:
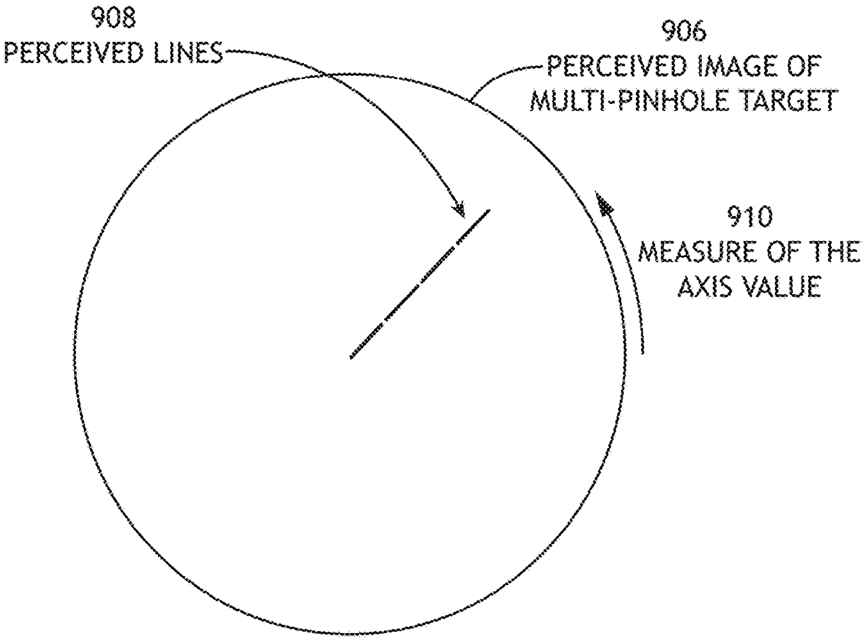
FIG. 9D is a simplified view of the multiple-pinhole target as perceived by the user with the astigmatism after the user adjusts the axis dial to align the two or more perceived lines associated with the two or more point light sources, in accordance with one or more embodiments of the present disclosure.

In some embodiments, the user may measure the orientation angle of astigmatism by rotating the multiple-pinhole target 902 (e.g., with an axis dial) to align the two or more perceived lines 908. FIG. 9C is a simplified view of the multiple-pinhole target 902 after the user adjusts an axis dial to align the two or more perceived lines 908 associated with the two or more point light sources 904, in accordance with one or more embodiments of the present disclosure. FIG. 9D is a simplified view of the multiple-pinhole target 902 as perceived by the user with the astigmatism after the user adjusts the axis dial to align the two or more perceived lines 908 associated with the two or more point light sources 904, in accordance with one or more embodiments of the present disclosure. For example, the user may rotate the multiple-pinhole target 902 (e.g., rotate the axis dial) until the two or more perceived lines 908 become continuously oriented into one longer line. An orientation angle of the multiple-pinhole target 902 may then provide a measure of the axis of the astigmatism in degrees 910 or axis value. It is contemplated herein that aligning the two or more perceived lines 908 associated with the two or more point light sources 904 may in some circumstances be easier and/or more accurate than characterizing an orientation angle from a single point light source.

The user may then rotate the power dial slowly in the direction of decreasing diopter values past the perceived reappearance of the two or more point light sources 904 until the two or more point light sources 904 appear to elongate parallel into the two or more perceived lines perpendicular to the angle previously recorded. The user may then take the difference of the setting of the power dial and the sphere value, indicating a measure of lens power prescribed to correct astigmatism or cylinder value.

FIG. 6 shows an optometer having two or more point light sources and a collimator to project images of the two or more point light sources onto the retina. However, the optometer in FIG. 6 does not include a focusing means to adjust the collimator. In this regard, such a configuration may allow a user to observe and assess refractive errors in the eye based on the size and shape of the image of the point source. In particular, the image of the point light source on the retina is evaluated at the limit of the eye's resolution.

Figure 10:
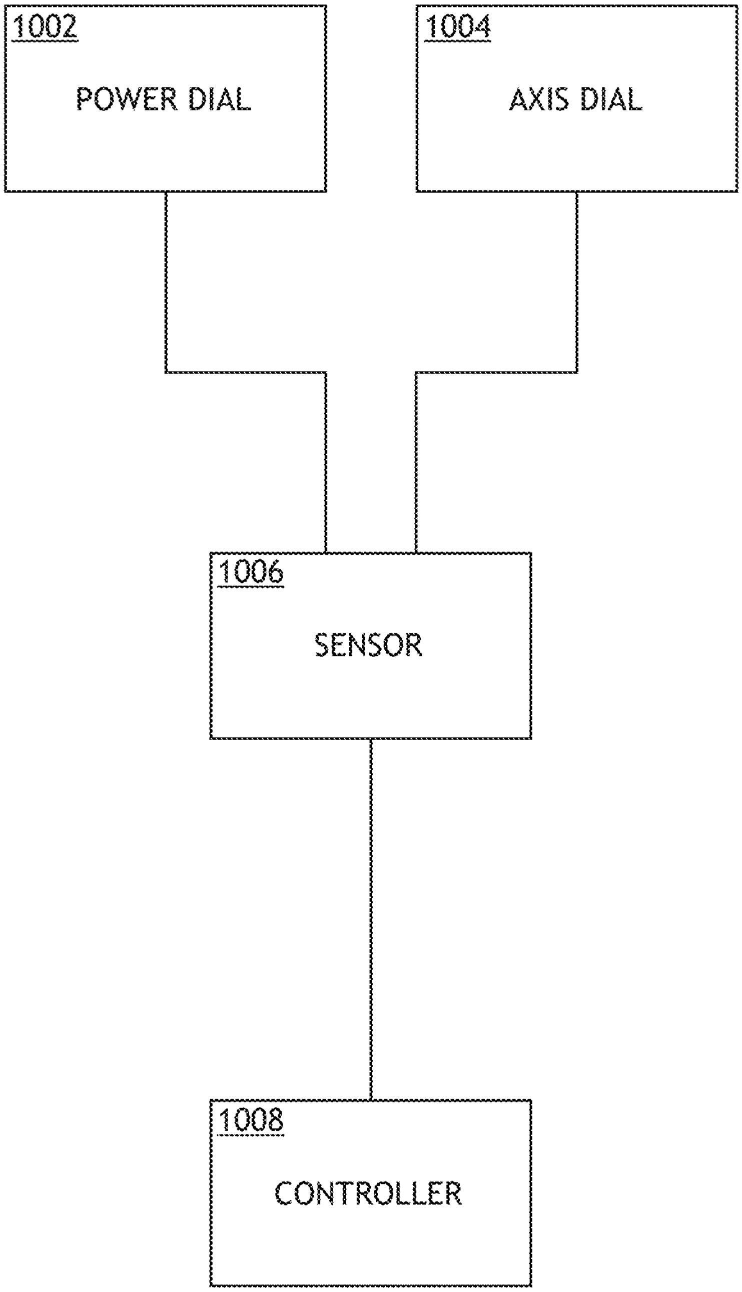
FIG. 10 is a simplified block diagram of the subjective optometer, in accordance with one or more embodiments of the present disclosure.

Referring now to FIG. 10, in some embodiments, the optometer includes one or more sensors 1006 to monitor positions of user-adjustable components. FIG. 10 is a simplified block diagram of the subjective optometer, in accordance with one or more embodiments of the present disclosure. In FIG. 10, the optometer may include, but is not limited to, either a power dial 1002 or an axis dial 1004 or both the power dial 1002 and the axis dial 1004. In this configuration, adjusting the power dial 1002 (e.g., use of the focusing means to focus, or a zoom lens to sharpen an image of the test object) or rotating the axis dial 1004 or both may be read manually or by the one or more sensors 1006 (e.g., one or more electronic sensors) which may be read by a controller 1008.

In some embodiments, the subjective optometer includes the controller 1008 with one or more processors configured to execute program instructions located on a memory (e.g., a memory device). The one or more processors of the controller 1008 may include any processing element known in the art. In this sense, the one or more processors may include the one or more sensors 1006 of any kind suitable for determining a position of an element in the optometer (e.g., a power dial 1002 to adjust a focusing means or an axis dial 1004 to rotate the multiple-pinhole target) to determine the relative position of the focusing means from its nominal position at a higher level of precision than achieved with subjective readings of manual position markings from a rotary dial or similar scale. For example, the one or more sensors 1006 may include, but is not limited to, magnetic (Hall effect), resistive (linear potentiometers), mechanical (piezoelectric), or optical (optical encoders) electronic sensors or encoders. Further, the memory may include any storage medium known in the art suitable for storing program instructions executable by the associated one or more processors. For example, the memory may include any non-transitory memory medium. As an example, the memory may include, but is not limited to, a read-only medium, a random-access memory, a magnetic or optical memory device (e.g., a disk), a magnetic tape, a solid-state drive and the like.

The program instructions may cause the processors to implement any number of steps. For example, the program instructions may cause the processors to receive data from the one or more sensors 1006 associated with settings of any of the one or more dials, and generate a prescription based on the data collected from the one or more sensors 1006. Further, the one or more sensors 1006 may be implemented into the optomechanical structure of the optometer to determine the position of the focusing means along the optical axis and coupled with the controller 1008 to calculate the indicated strength in diopters of the necessary amount of correction. In this regard, the focusing means can adjust the separation distance between the collimator lens and the test object by adjusting the position of at least one of the collimator lens or the test object. Further, the one or more sensors can be configured to determine a rotational position of the test object (e.g., a multiple-pinhole target). The corrective data (e.g., prescription data) should include any type of information suitable for fabricating corrective eyewear (e.g., eyeglasses, contact lenses, or the like) and may include, but is not limited to, sphere value, cylinder value, or axis value information. The corrective data may be displayed on a display device (e.g., a small electronic display). The display device may be any kind suitable for displaying visual information (e.g., LED display, OLED display, LCD display, and the like). The display device may also guide the user through the process of operating the optometer. It is to be understood, however, that the one or more sensors 1006, as illustrated in FIG. 10, may be added to any embodiment, not just one that includes a multiple-pinhole target.

It is to be understood that FIGS. 1-10, as well as the associated descriptions, are provided solely for illustrative purposes and should not be interpreted as limiting. For example, an optometer in accordance with the present disclosure need not include all features indicated in FIGS. 1-10.

The subjective optometer disclosed herein is sufficiently low in cost making it affordable for most households. Measurements can be made at the convenience and practicality of the home setting, where working conditions and needed darkness are readily available. It readily provides multiple types of robust measurements needed for a prescription for ordering glasses online and/or by mail. The optometer can also be used to check current prescription glasses as well as track developing changes in vision like myopia in children and presbyopia in adults.

The subjective optometer disclosed herein is of sufficient accuracy and reliability for ordering prescription glasses online and/or by mail, which greatly increases the availability and affordability. Additionally, the ability to provide an assessment that is precise to the limit of the vision of the patient is very useful. It will timely show the tendencies in the development of the refractive errors of the eye due to usage, child development and aging. Other benefits of this optometer are the ability to track the results of a test procedure, remedies and medical conditions. The present disclosure provides a subjective optometer to address these needs. Means to electronically record the results may be added to the optometer as an option. Home use indicates that:

- The device can be reliably operated by the average adult.
- The measurement is reliable for making an important decision, like ordering prescription glasses online and/or by mail.
- The device can be mass-produced at an affordable cost for the average household.

The advantages of this arrangement are summarized as follows:

- Measurements can be made with the eye at the rest position, that is at total darkness, which is an essential requirement for reliable and repeatable values. Cycloplegia and dilation medicines are not needed.
- Measurements can also be made under active circumstances if so desired, by activation of a different part of the test object and by making use of the various home conditions.
- Measurements are made with an accuracy that makes full use of the resolution capability of the eye. An accuracy of 0.12 D is readily achievable and 0.08 D after some practice. The measurement criterion when using a point source, which is the minimum line width, is very nearly objective, as compared to the subjective "best picture" opinion of the patient with the optometrist. Also, the use of a resolution target (e.g., a USAF-1951 Airforce Resolution Chart) is considered to be close to being objective.

Defocus is shown as a circle and astigmatism as a line, together forming an illuminated undetailed area that does not trigger the eye to accommodate.

The full aperture of the pupil can be engaged because the overall light input is very small. The refractive errors are measured in otherwise total darkness. Measurements can also be made under actual lighting conditions, which reduces the pupil size. The test environment can be accurately controlled by a numerical control of the light intensity, the numerical aperture of the light source and the color of the test object illumination.

The accuracy is sufficiently high in order to timely observe small changes due to working conditions, like excessive close-up activity that may cause myopia, tests, experiments, medicines, circumstances and medical conditions.

Accurate chromatic aberrations can be measured by a change of color of the point source.

The present optometer is not limited by a finite step size.

The subjective optometer disclosed herein can be executed as an inexpensive compact personal unit or as a high accuracy research tool.

What is claimed:

1. An optometer comprising:

a test object including one or more point light sources; and a collimator lens configured to direct light from the one or more point light sources to an eye of a user to allow the eye to generate images of the one or more point light sources on a retina of the eye when the eye is in a rest position without triggering the eye to focus, wherein a separation distance between the collimator lens and the test object is adjustable by the user, wherein a difference between a user-selected position of the collimator lens with respect to the test object providing in-focus images of the one or more point light sources as determined by the user and a nominal position of the collimator lens with respect to the test object providing collimated light from the one or more point light sources to the eye is indicative of visual refractive error of the user.

2. The optometer of claim 1, wherein the visual refractive error of the user represents combined refractive error in the eye of the user and a corrective lens when the user views the test object with the corrective lens.

3. The optometer of claim 1, wherein the collimator lens includes a zoom lens.

4. The optometer of claim 1, wherein the images of the one or more point light sources on the retina correspond to one or more circles at the user-selected position providing the in-focus images of the one or more point light sources when the eye is free of astigmatism, wherein the user-selected position providing the in-focus images of the one or more point light sources correspond to a position at which the one or more circles has a minimum observable diameter by the user.

5. The optometer of claim 1, wherein the images of the one or more point light sources on the retina correspond to one more lines at two positions of the collimator lens with respect to the one or more point light sources when the eye includes astigmatism, wherein a difference between the two positions provides a measurement of a magnitude of the astigmatism.

6. The optometer of claim 5, wherein the test object further comprises:

a rotational orientation mark, wherein a user-identified direction of the rotational orientation mark providing a smallest line width of the rotational orientation mark as determined by the user is indicative of an orientation of astigmatism in the eye.

7. The optometer of claim 1, wherein at least one of an intensity, a numerical aperture, or a spectrum of the one or more point light sources is adjustable.

8. The optometer of claim 1, wherein the one or more point light sources comprises a single point light source.

9. The optometer of claim 1, wherein the one or more point light sources comprises two or more point light sources.

10. The optometer of claim 9, wherein the two or more point light sources are arranged in a line, wherein the test object is rotatable by the user, wherein a presence of astigmatism is determinable when the user perceives the two or more point light sources as two or more lines at one or more positions of the collimator lens, wherein an axis of astigmatism is associated with an orientation angle of a target at which the two or more lines are aligned.

11. The optometer of claim 10, wherein the separation distance between the collimator lens and the test object is adjustable by the user, wherein the optometer further comprises:

one or more sensors configured to determine the separation distance and further configured to determine a rotational position of the test object;

a controller including one or more processors configured to execute program instructions causing the one or more processors to determine corrective data based on the separation distance and the rotational position of the test object from the one or more sensors, wherein the corrective data includes at least one of a sphere value, a cylinder value, or an axis value; and a display device to display the corrective data.

12. The optometer of claim 1, wherein the separation distance between the collimator lens and the test object is adjustable by the user, wherein the optometer further comprises:

one or more sensors configured to determine the separation distance;

a controller including one or more processors configured to execute program instructions causing the one or more processors to determine corrective data based on the separation distance from the one or more sensors, wherein the corrective data includes a sphere value; and a display device to display the corrective data.

13. An optometer comprising:

a test object including one or more point light sources; and a zoom lens configured to direct light from the one or more point light sources to an eye of a user to generate images of the one or more point light sources on a retina of the eye when the eye is in a rest position without triggering the eye to focus, wherein the zoom lens provides adjustable focusing of the test object, wherein a nominal configuration of the zoom lens provides collimated light from the one or more point light sources to the eye of the user, wherein a user-selected configuration of the zoom lens providing in-focus images of the one or more point light sources is indicative of visual refractive error of the user.

14. The optometer of claim 13, wherein the visual refractive error of the user represents combined refractive error in the eye of the user and a corrective lens when the user views the test object with the corrective lens.

15. The optometer of claim 13, wherein the images of the one or more point light sources on the retina correspond to one or more circles at the user-selected configuration providing the in-focus images of the one or more point light sources when the eye is free of astigmatism, wherein the user-selected configuration of the zoom lens providing the in-focus images of the one or more point light sources correspond to a position at which the one or more circles has a minimum observable diameter by the user.

16. The optometer of claim 13, wherein the images of the one or more point light sources on the retina correspond to one or more lines at two configurations of the zoom lens when the eye includes astigmatism, wherein a difference between the two configurations provides a measurement of a magnitude of the astigmatism.

17. The optometer of claim 13, wherein the test object further comprises:

a rotational orientation mark, wherein a user-identified direction of the rotational orientation mark providing a smallest line width of the rotational orientation mark as determined by the user is indicative of an orientation of astigmatism in the eye.

18. The optometer of claim 13, wherein at least one of an intensity, a numerical aperture, or a spectrum of the one or more point light sources is adjustable.

19. The optometer of claim 13, wherein the one or more point light sources comprises a single point light source.

20. The optometer of claim 13, wherein the one or more point light sources comprises two or more point light sources.

21. The optometer of claim 20, wherein the two or more point light sources are arranged in a line, wherein at least one of the test object or the zoom lens is rotatable by the user, wherein a presence of astigmatism is determinable when the user perceives the two or more point light sources as two or more lines at one or more positions of the zoom lens, wherein an axis of astigmatism is associated with an orientation angle of a target at which the two or more lines are aligned.

22. The optometer of claim 21, further comprising:

one or more sensors configured to determine a position of the zoom lens and a rotational position of at least one of the test object or the zoom lens;

a controller including one or more processors configured to execute program instructions causing the one or more processors to determine corrective data based on the position of the zoom lens and the rotational position of at least one of the test object or the zoom lens from the one or more sensors, wherein the corrective data includes at least one of a sphere value, a cylinder value, or an axis value; and a display device to display the corrective data.

23. The optometer of claim 13, further comprising:

one or more sensors configured to determine a position of the zoom lens;

a controller including one or more processors configured to execute program instructions causing the one or more processors to determine corrective data based on the position of the zoom lens from the one or more sensors, wherein the corrective data includes a sphere value; and a display device to display the corrective data.

* * * * *